(12) United States Patent
Wiggin et al.

(10) Patent No.: US 11,969,218 B2
(45) Date of Patent: Apr. 30, 2024

(54) AUGMENTED REALITY SURGERY SET-UP FOR ROBOTIC SURGICAL PROCEDURES

(71) Applicant: Asensus Surgical US, Inc., Durham, NC (US)

(72) Inventors: Michael Bruce Wiggin, Raleigh, NC (US); Kevin Andrew Hufford, Cary, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

(21) Appl. No.: 17/368,747

(22) Filed: Jul. 6, 2021

(65) Prior Publication Data

US 2022/0000558 A1 Jan. 6, 2022

Related U.S. Application Data

(60) Provisional application No. 63/048,183, filed on Jul. 5, 2020.

(51) Int. Cl.
| | | |
|---|---|---|
| *A61B 34/10* | (2016.01) | |
| *A61B 34/00* | (2016.01) | |
| *G06T 7/73* | (2017.01) | |
| *G06V 20/20* | (2022.01) | |

(52) U.S. Cl.
CPC .............. *A61B 34/10* (2016.02); *A61B 34/25* (2016.02); *G06T 7/73* (2017.01); *G06V 20/20* (2022.01); *A61B 2034/104* (2016.02); *A61B 2034/105* (2016.02); *A61B 2034/254* (2016.02)

(58) Field of Classification Search
CPC ... A61B 34/10; A61B 2034/254; A61B 34/25; A61B 2034/104
USPC .......................................................... 345/633
See application file for complete search history.

(56) References Cited

U.S. PATENT DOCUMENTS

| | | | |
|---|---|---|---|
| 10,410,746 B2 | 9/2019 | Moctezuma de la Barrera et al. | |
| 2003/0144765 A1* | 7/2003 | Habibi .................. | G06T 1/0007 700/259 |
| 2004/0172168 A1* | 9/2004 | Watanabe .............. | B25J 9/1664 700/264 |
| 2004/0186627 A1* | 9/2004 | Watanabe ............ | G05B 19/425 700/264 |
| 2006/0229766 A1* | 10/2006 | Setsuda ................ | G05B 19/425 700/245 |
| 2007/0005045 A1 | 1/2007 | Mintz et al. | |
| 2007/0083098 A1 | 4/2007 | Stern et al. | |

(Continued)

FOREIGN PATENT DOCUMENTS

WO WO-2014094717 A1 * 6/2014 ......... A61B 1/00149

*Primary Examiner* — Javid A Amini

(57) ABSTRACT

A system and method provide feedback to guide a user to arrange components of a surgical robotic system in a suitable arrangement for the surgical procedure to be performed. An image of a medical procedure site at which a robotic manipulator and a second object such as a second robotic manipulator, patient table, patient, and bedside staff are located. The image is displayed for a user. The system uses computer vision to recognize the robotic manipulator and second object in the image and determine their relative positions. Based on the type of surgical procedure that is to be performed, the system determines a target position for the robotic manipulator and/or the second object, and displays, as an overlay to the displayed image, a graphical indication of the target position.

7 Claims, 4 Drawing Sheets

(56) References Cited

U.S. PATENT DOCUMENTS

| | | |
|---|---|---|
| 2012/0101508 A1* | 4/2012 | Wook Choi ........... B25J 9/1697 |
| | | 700/259 |
| 2012/0307027 A1 | 12/2012 | Popovic et al. |
| 2013/0066335 A1 | 3/2013 | Barwinkel et al. |
| 2015/0297313 A1 | 10/2015 | Reiter et al. |
| 2017/0079722 A1 | 3/2017 | O'Grady et al. |
| 2017/0239000 A1* | 8/2017 | Moctezuma de la Barrera .......... |
| | | G16H 40/40 |
| 2017/0333137 A1 | 11/2017 | Roessler |
| 2019/0069962 A1* | 3/2019 | Tabandeh ............... A61B 34/30 |
| 2020/0054412 A1* | 2/2020 | Fuerst ................... A61B 17/00 |
| 2020/0205911 A1* | 7/2020 | Hufford ................. A61B 34/20 |
| 2021/0153958 A1* | 5/2021 | Meglan ................... B25J 5/007 |

* cited by examiner

AUGMENTED REALITY SURGERY SET-UP FOR ROBOTIC SURGICAL PROCEDURES

BACKGROUND

There are various types of surgical robotic systems on the market or under development. Some surgical robotic systems use a plurality of robotic arms. Each arm carries a surgical instrument, or the camera used to capture images from within the body for display on a monitor. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

In some surgical robot systems, the arms are mounted on one or more bases moveable along the floor in the surgical suite. For example, the Senhance Surgical System marketed by Asensus Surgical, Inc. uses a plurality of separate robotic arms, each carried on a separate base. In other systems, a first base might carry a first pair of arms, and a second base might carry one or more additional arms. In either case, the necessary position of the arms (and thus their bases) relative to the patient bed in the surgical suite is dependent on the procedure to be carried out.

This application describes a system and method that facilitates arm positioning and set-up prior to or during surgery. Use of these features can reduce the amount of personnel time and surgical suite time spent performing these tasks, and, therefore, reduce the procedure cost of the surgery.

DETAILED DESCRIPTION

Figure 1:
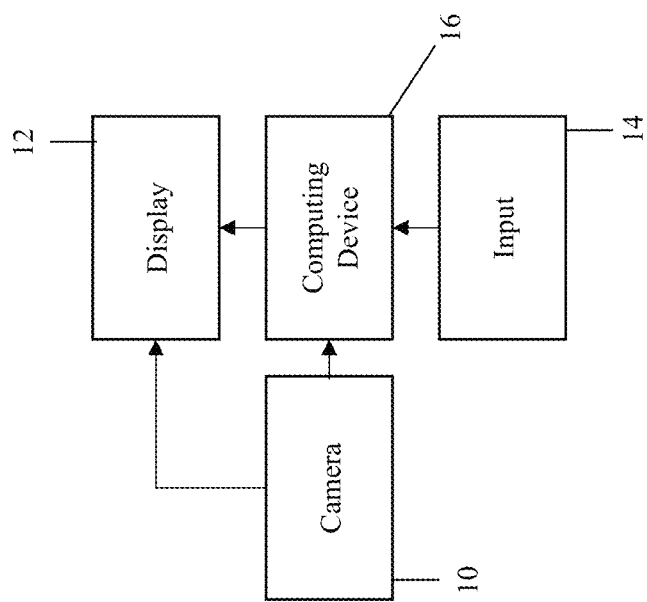
FIG. 1 is a schematic diagram illustrating components of the disclosed system.

Referring to FIG. 1, a system for providing feedback to guide setup of a surgical robotic system includes at least one camera 10 positionable to capture an image of a medical procedure site. An image display 12 displays the captured image. A user input 14 is used to give input to the system that is pertinent to the surgical set-up. The input may indicate the type of surgery, patient data such as body mass index (BMI), the numbers and/or types of bedside personnel, the lengths of instruments to be mounted to the surgical system, the viewing angle of the endoscope to be used for the procedure. At least one processor 16 is configured to receive the procedure-related input comprising a surgical procedure type;

display the image in real time on an image display;

use computer vision to recognize at least one of the first subject and the second subject in the image and to determine the relative positions of the first subject and the second subject, determine, based on the procedure-related input, a target position of at least one of the first subject and the second subject within the medical procedure site, and display, as an overlay to the displayed image, a graphical indication of the target position.

First Embodiment

In a first embodiment, the system comprises at least one camera 10 for capturing images of a medical procedure site within a surgical suite. The medical procedure site is typically one at which at least two of the following subjects are positioned: a first robotic manipulator, a second robotic manipulator, a patient table, a patient, and one or more members bedside staff. The system also includes an image display 12 that displays the images, and one or more input devices 14. A processor 16 is configured for receiving the images and other data (including from the input devices 14) regarding the type of procedure to be performed, patient metrics (e.g. gender, height, body mass index (BMI)), bed parameters (e.g. height, Trendelenburg/reverse Trendelenburg angle), instrument parameters (e.g. the operative lengths of instruments to be used on the arms, endoscope angle etc.). The processor is further configured to generate overlays on the image display to assist the operating room staff in setting up for a robotic surgery case. More specifically, augmented reality is used to project an overlay, which may be a 3D overlay, of an optimized system setup for the robotic surgery case over the real-time display of the robotic arms. This graphical display may provide outlines of optimal robotic manipulator base placement, with the current location of the robotic manipulator bases also displayed, providing real-time feedback to the users as they wheel the bases into the correct positions and orientations. The display may change or other visual or optical feedback may be given as the correct positions are achieved. Operating room staff reference the overlays while positioning the robotic arms in order to accurately position the robotic system in place to prepare for the operation.

The above-described features may be those of a device such as a tablet or smart phone, with the device's touch screen, microphone and/or one or more other devices (e.g. keyboard, mouse, stylus) used as the user input device 14. In some embodiments, the camera may be integrated with those devices or separate from them. Images from the integrated camera may be supplemented by image data captured from one or more external cameras disposed at one or more locations within the operating room.

Using surgical simulation, optimized setup locations for the Senhance System's arms were established for different surgical procedures. These positions ensure the arm does not enter limited motion and prevents arm collision during surgery. In order to quickly communicate how to position the arms and trocars, data from the simulations were developed into an augmented reality app incorporating the features described above. In use, the user holds a device (smart phone or tablet) programmed with this app so that the camera of the device captures real time images of the robotic arms. After the user inputs the relevant instrument, patient, bed, procedure etc. data, the app generates and displays an overlay that shows the users the ideal position of the arms (the "AR arms") and trocars in the operating room. Operating room staff can then use the app to match the physical arms viewed on the image display with the AR arms.

Figure 2:
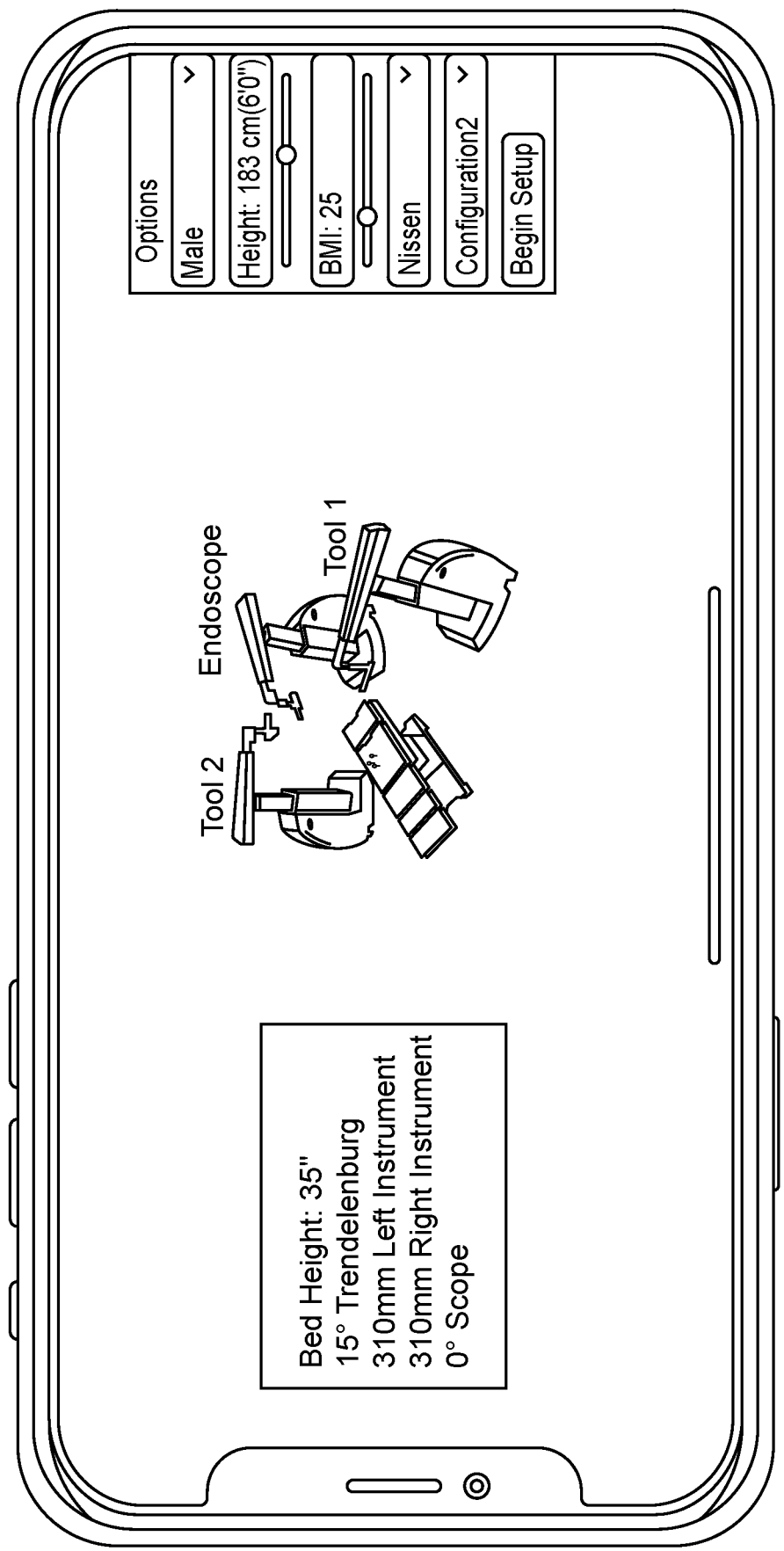
FIG. 2 is a screen capture of an input screen displayed on the display according to a first embodiment.

FIG. 2 shows a screen capture of the user interface (display) where the patient information is selected, the procedure (Nissen) is selected. A variety of options for arrangements of arms, table etc. for the selected procedure may be displayed to the user, and the user may use the input device to select a configuration that best fits into their operating suite.

Figure 3:
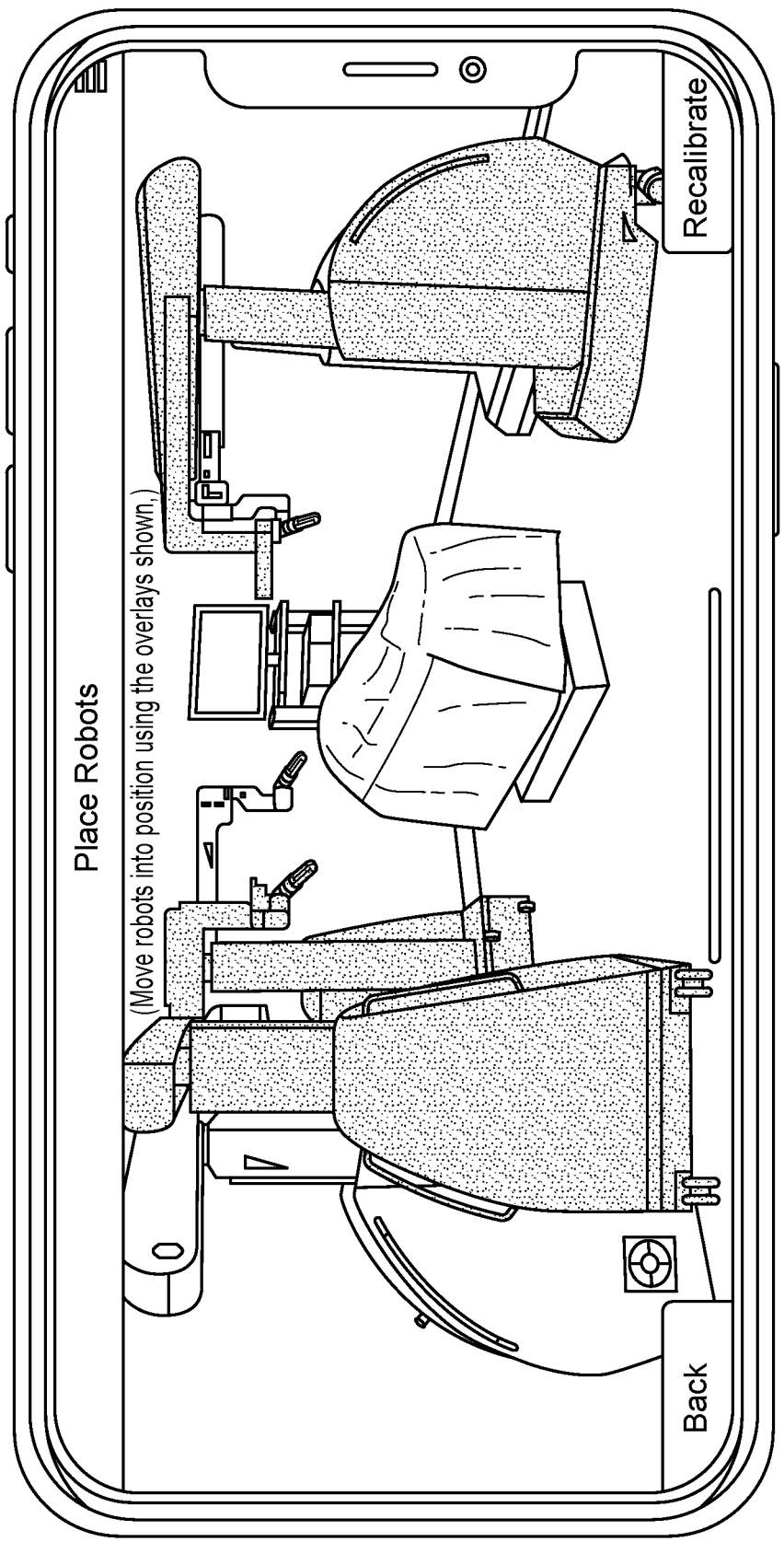
FIG. 3 is a screen capture of an instruction screen displayed on the display according to the first embodiment.
Figure 4:
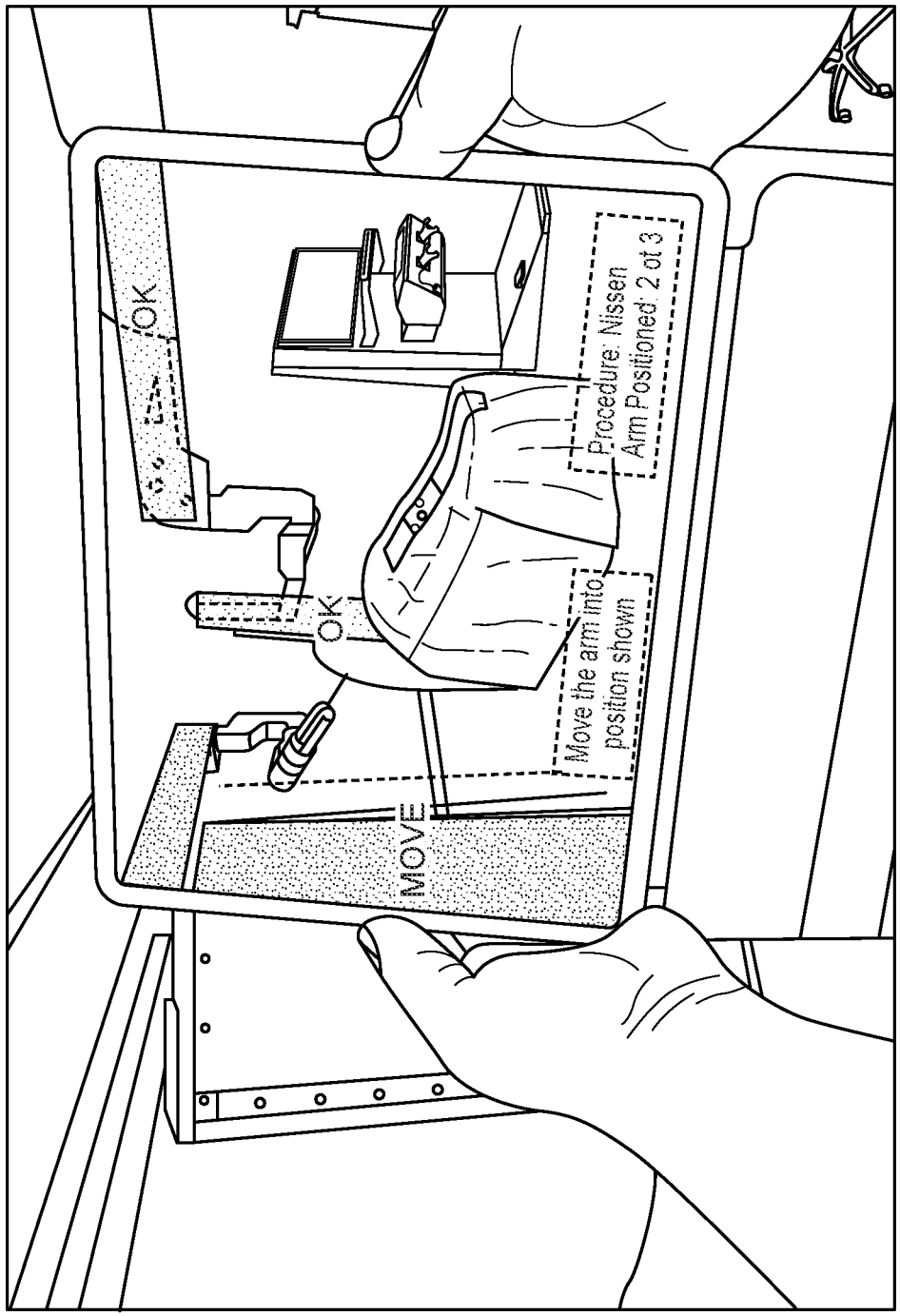
FIG. 4 is a screen capture of an instruction screen displayed on the display according to the second embodiment.

FIG. 3 shows a screen capture showing the view of the operating room captured by the device's camera as displayed on the device's image display, with overlaid AR arms shown in blue. The OR staff can then position the actual arms to overlap and align with the displayed AR arms.

In many cases optimal robotic base placement will be dependent on the target procedures. The system may include a database of known procedures and optimal placements of the arms for those parameters, optimally cross-referenced with other metrics such as patent BMI, instrument length, etc. In other embodiments, the processor may be configured to determine the procedure placement automatically based on user input of trocar locations or based on automatic recognition of trocar locations via the referenced cameras or other sources.

The system and method allow the user to quickly and accurately setup a robotic surgical system such as the Senhance System without the need for measuring devices and ensures the arms are set up accurately.

In other embodiments, alternative forms of feedback may be given to the user about placement, including GUI, auditory signals, and/or projection of base positions onto the floor of the operating room using ceiling-mounted or boom-mounted lights.

Second Embodiment

A second embodiment is similar to the first embodiment, but may further provide on-screen instructions directing the user to move a particular arm to ensure optimal positioning (see the AR arm shown on the left of the display below, which is depicted in red, is marked with the word "move," and includes the notation "move arm into position shown." The AR overlays on the arms displayed in the center and to the right of the display are green and marked with the word "ok," indicating that those arms are correctly positioned.

Third Embodiment

A third embodiment incorporates features similar to those described above but makes use of an augmented reality headset to provide guidance and overlays to assist with proper placement. In this configuration, a virtual reality headset with external-view cameras might be use. Alternatively, transparent/translucent augmented reality headset or glasses may be used.

The examples given above describe use of the system/method for positioning of robotic arms, but it should be appreciated that they may also be used to position other equipment as well as operating room personnel, including any of the following in any combination with the robotic arms: the patient, bedside staff, the patient, the OR table.

Any of the described embodiments may be modified to, in lieu of or in addition to providing feedback to the user to guide the user's placement of the robotic manipulators and other components/personnel, the system and method may be used for any of the following:

Initiating automatic motion of robotic manipulator bases to a desired position.

Displaying recommendations to the user about moving other elements (booms, laparoscopic column, etc.) within the operating room to alternate locations.

Initiating, or displaying recommendations to the user about, intra-operative adjustments or recommendations for adjustments to the surgical system Concepts described in co-pending and commonly owned U.S. application Ser. No. 16/733,200, entitled Determining Relative Robot Base Positions Using Computer Vision, incorporated herein by reference may be combined with the concepts described in this application. For example, the methods and configurations used to determine the current relative positions of manipulator bases may be used in conjunction with the concepts described here.

We claim:

1. A method for providing feedback to guide setup of a surgical robotic system, the method comprising the steps of:
   receiving an image of a medical procedure site in which at least one first subject comprising a first robotic manipulator, and at least one second subject comprising at least one of a second robotic manipulator, patient table, patient, and bedside staff are located;
   receiving, from a user input device, procedure-related input comprising a user designation of a type of surgical procedure to be performed;
   displaying the image in real time on an image display;
   using computer vision to recognize at least one of the first subject and the second subject in the image and to determine the relative positions of the first subject and the second subject;
   displaying, as an overlay to the displayed image, a graphical indication of a target position of at least one of the first subject and the second subject within the medical procedure site, the target position determined based on the procedure-related input, and
   displaying, as an overlay to the displayed image, a graphical indication of a trocar target position within the medical procedure site, wherein the trocar target position comprises a recommended position for a trocar to be used to receive a surgical instrument carried by the first robotic manipulator, and is determined based on the procedure-related input, wherein said graphical indication is displayed before a user positions the trocar through patient tissue.

2. The method of claim 1, wherein the method includes retrieving preferred relative positions of the first subject and the second subject from a database based on the procedure-related input and determining the target position based on the preferred relative positions.

3. The method of claim 1, wherein the determining step determines the relative 3D positions of the first subject and the second subject.

4. A system for providing feedback to guide setup of a surgical robotic system, the system comprising:
   at least one camera positionable to capture an image of a medical procedure site in which at least one first subject comprising a first robotic manipulator, and at least one second subject comprising at least one of a second robotic manipulator, patient table, or patient are located;
   an image display;
   a user input device operable by a user to designate procedure-related input corresponding to a type of surgical procedure to be performed;
   at least one processor configured to receive the procedure-related input;

display the image in real time on an image display;

use computer vision to recognize at least one of the first subject and the second subject in the image and to determine the relative positions of the first subject and the second subject, determine, based on the procedure-related input, a target position of at least one of the first subject and the second subject within the medical procedure site, determine, based on the procedure-related input, a recommended trocar target position within the medical procedure site, wherein the recommended trocar target position comprises a position for a trocar to be used to receive a surgical instrument carried by the first robotic manipulator, and display, as an overlay to the displayed image, a graphical indication of the recommended target position and the trocar target position.

5. The system of claim 4, where the system further includes a database, and wherein the at least one processor is configured to retrieve preferred relative positions of the first subject and the second subject from a database based on the procedure-related input and to determine the target position based on the preferred relative positions.

6. The system of claim 4, where the processor is configured to determine the relative 3D positions of the first subject and the second subject based on image data from the image.

7. The system of claim 4, wherein said at least one processor is configured to:

determine, based on the procedure-related input, a target trocar position for a trocar to be used to receive a surgical instrument carried by the first robotic manipulator, and display, as an overlay to the displayed image, a graphical indication of the target trocar position.

* * * * *